United States Patent
Gauchet et al.

(10) Patent No.: US 6,733,532 B1
(45) Date of Patent: *May 11, 2004

(54) INTERVERTEBRAL DISC PROSTHESIS WITH IMPROVED MECHANICAL BEHAVIOR

(75) Inventors: Fabien Gauchet, Duvy (FR); Régis Le Couedic, Cestas (FR)

(73) Assignee: Stryker Spine (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/857,726

(22) PCT Filed: Dec. 9, 1999

(86) PCT No.: PCT/FR99/03073

§ 371 (c)(1),
(2), (4) Date: Jul. 20, 2001

(87) PCT Pub. No.: WO00/35385

PCT Pub. Date: Jun. 22, 2000

(30) Foreign Application Priority Data

Dec. 11, 1998 (FR) .............................. 98 15672

(51) Int. Cl.⁷ .................................................. A61F 2/44
(52) U.S. Cl. ............................... 623/17.12; 623/17.13; 623/17.14; 606/61
(58) Field of Search .................... 623/17.11, 17.12, 623/17.13, 17.14, 17.15, 17.16; 606/61, 72, 73, 86, 87

(56) References Cited

U.S. PATENT DOCUMENTS

| 3,867,728 A | 2/1975 | Stubstad et al. |
|---|---|---|
| 3,875,595 A | 4/1975 | Froning |
| 4,743,256 A | 5/1988 | Brantigan |
| 4,863,477 A | 9/1989 | Monson |
| 4,911,718 A | 3/1990 | Lee et al. |
| 4,932,969 A | 6/1990 | Frey et al. |
| 5,002,576 A | 3/1991 | Fuhrmann et al. |
| 5,071,437 A | 12/1991 | Steffee |
| 5,123,926 A | 6/1992 | Pisharodi |
| 5,397,364 A | 3/1995 | Kozak et al. |
| 5,401,269 A * | 3/1995 | Buttner-Janz et al. ........ 623/17 |
| 5,425,773 A | 6/1995 | Boyd et al. |
| 5,507,816 A | 4/1996 | Bullivant |
| 5,534,028 A | 7/1996 | Bao et al. |
| 5,556,431 A | 9/1996 | Buttner-Janz et al. |
| 5,609,635 A | 3/1997 | Michelson |
| 5,674,294 A | 10/1997 | Bainville et al. |
| 5,676,701 A | 10/1997 | Yuan et al. |
| 5,683,465 A | 11/1997 | Shinn et al. |
| 5,782,832 A | 7/1998 | Larsen et al. |

(List continued on next page.)

FOREIGN PATENT DOCUMENTS

| DE | 22 63 842 | 12/1972 |
|---|---|---|
| DE | 3741493 | 6/1989 |
| DE | 3 939 593 | 6/1991 |
| EP | 0 277 282 | 10/1987 |
| EP | 0642775 A1 | 9/1994 |
| FR | 2 723 841 | 8/1994 |
| FR | 2 728 037 | 6/1996 |
| WO | WO-96/01598 | 7/1995 |

OTHER PUBLICATIONS

U.S. patent application Ser. No. 09/857,659, Gauchet et al., filed Jul. 20, 2001.
International Search Report.

*Primary Examiner*—Nicholas D. Lucchesi
*Assistant Examiner*—Quang D Thanh
(74) *Attorney, Agent, or Firm*—Lerner, David, Littenberg, Krumholz & Mentlik, LLP

(57) ABSTRACT

An intervertebral disc prosthesis comprising two plates and a cushion interposed between the plates is contemplated. The cushion includes a compressible body having two ends in contact with the plates. At least one of the ends is freely displaceable relative to the plate in a parallel direction. Thus, the prosthesis imitates and approximates the mechanical properties of a healthy natural intervertebral disc.

23 Claims, 3 Drawing Sheets

U.S. PATENT DOCUMENTS

| | | |
|---|---|---|
| 5,824,094 A | 10/1998 | Serhan et al. |
| 5,865,846 A | 2/1999 | Bryan et al. |
| 5,888,226 A | 3/1999 | Gogozinski |
| 6,052,992 A | 4/2000 | Erochenko |
| 6,093,205 A * | 7/2000 | McLeod et al. ......... 623/17.16 |
| 6,117,174 A | 9/2000 | Nolan |
| 6,136,031 A | 10/2000 | Middleton |
| 6,162,252 A | 12/2000 | Kuras et al. |
| 6,179,838 B1 | 1/2001 | Fiz |
| 6,187,043 B1 | 2/2001 | Ledergerber |
| 6,228,118 B1 | 5/2001 | Gordon |
| 6,348,071 B1 | 2/2002 | Steffe et al. |
| 6,447,547 B1 | 9/2002 | Michelson |
| 6,527,804 B1 * | 3/2003 | Gauchet et al. .......... 623/17.12 |
| 6,582,468 B1 * | 6/2003 | Gauchet .................. 623/17.16 |

\* cited by examiner

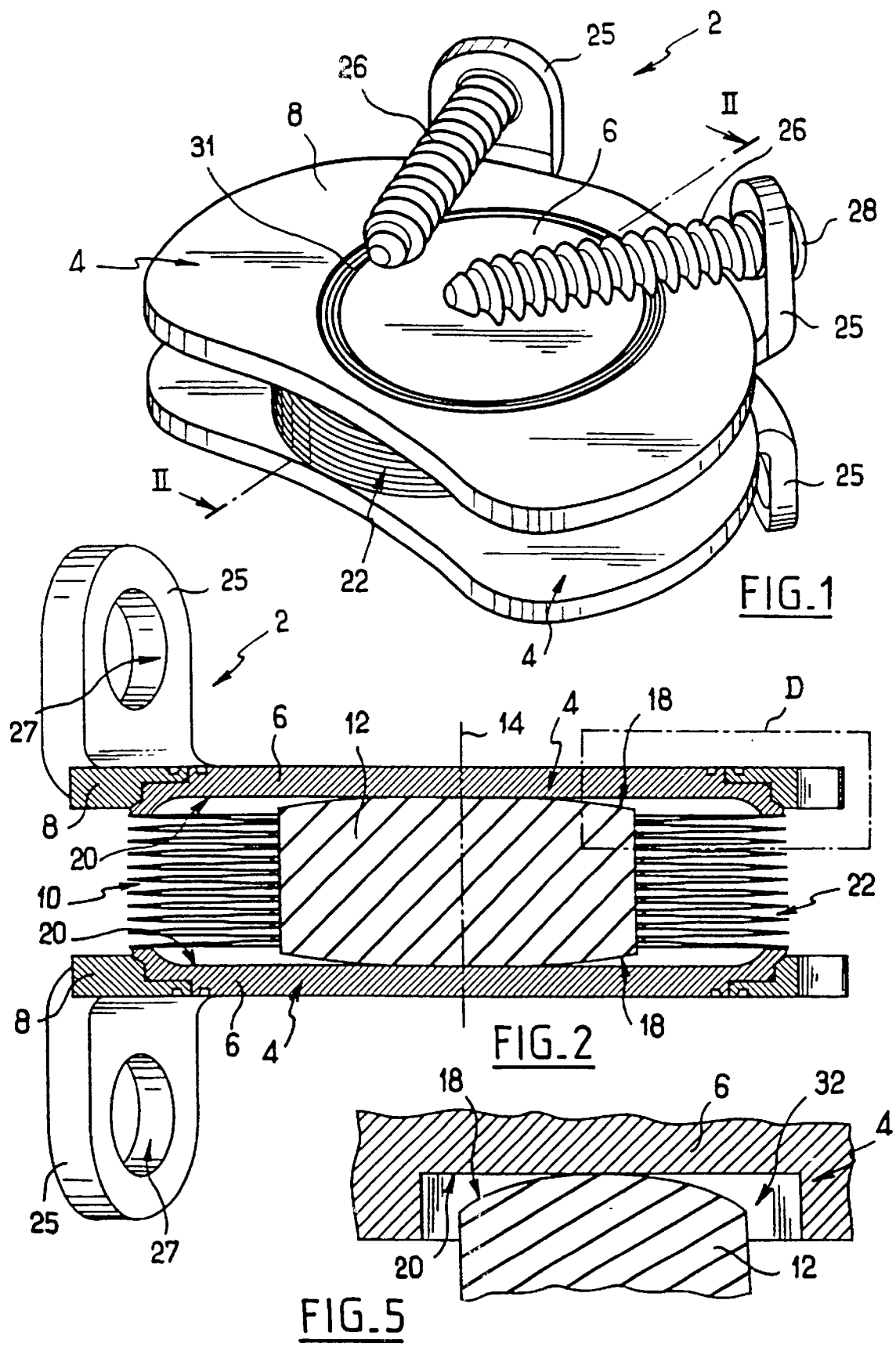

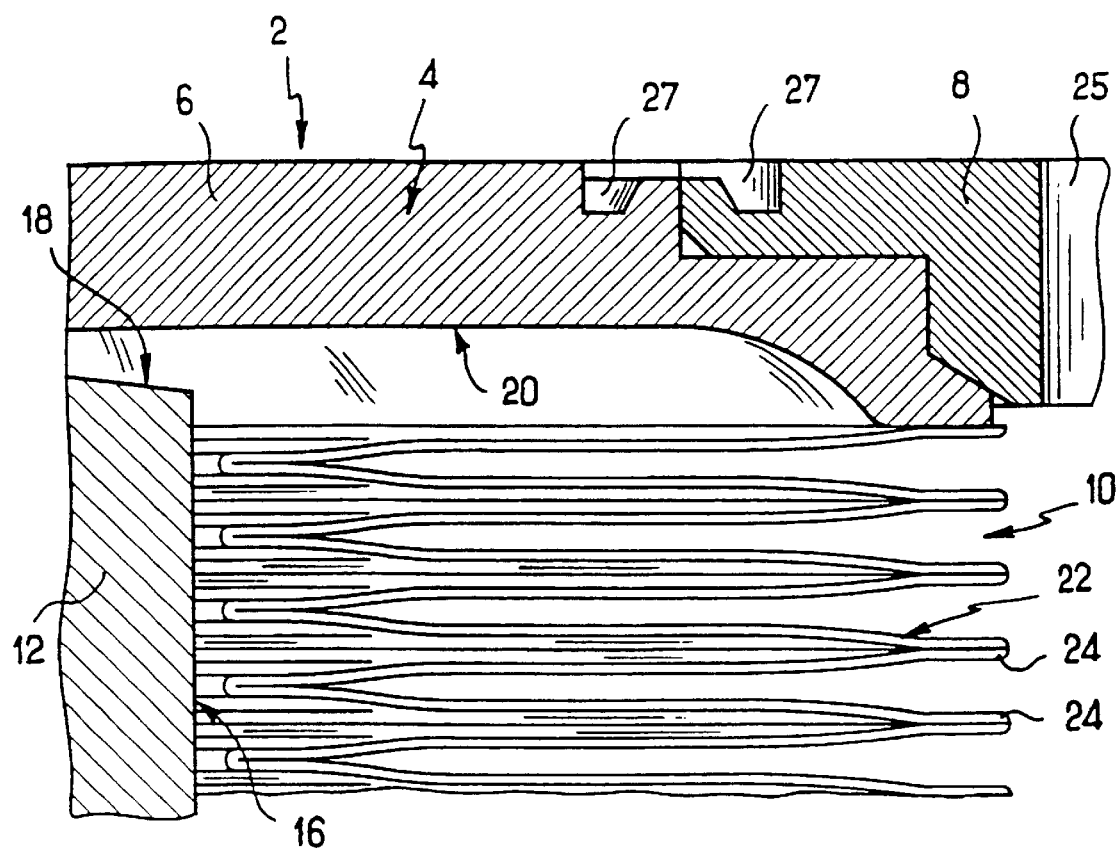
FIG_3
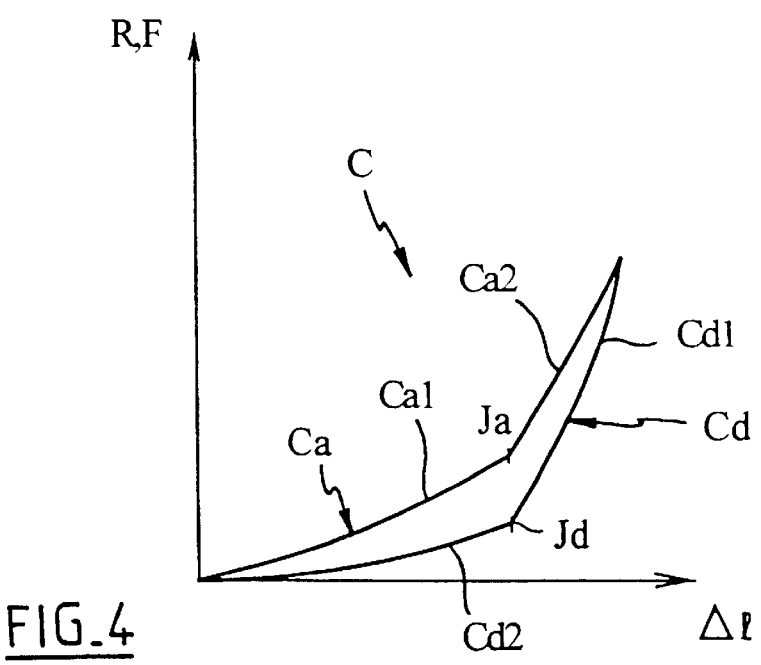
FIG_4

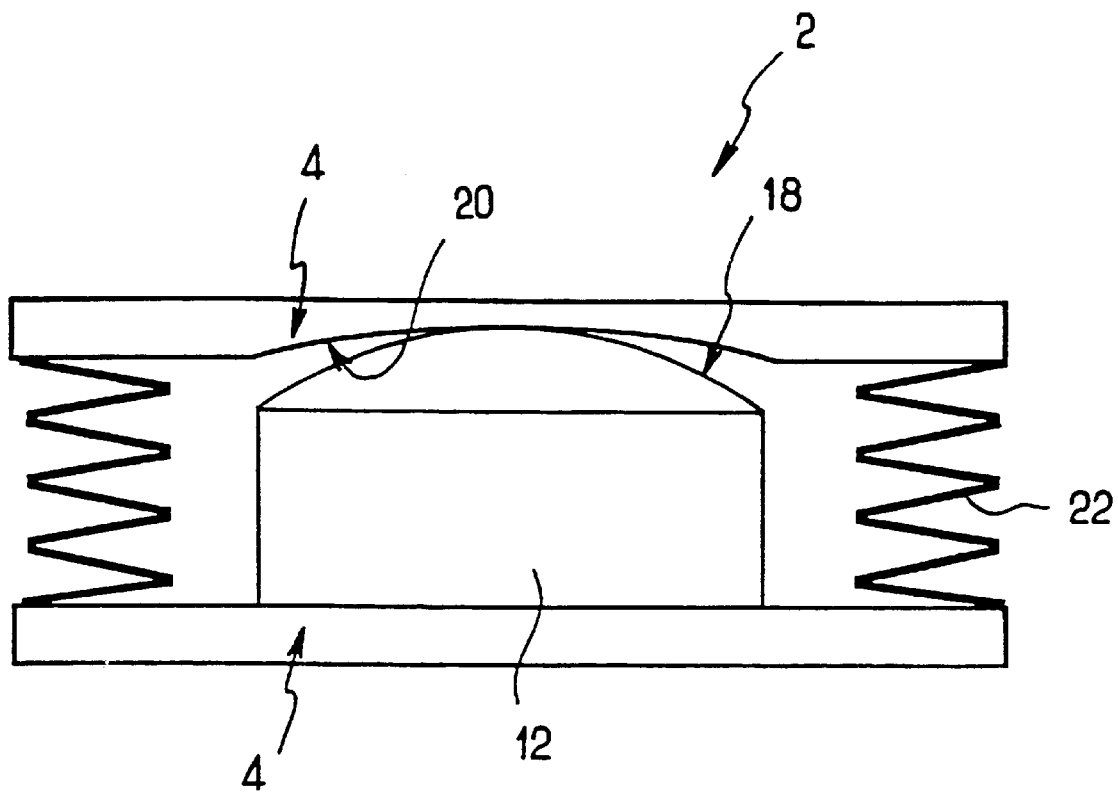
FIG_6

INTERVERTEBRAL DISC PROSTHESIS WITH IMPROVED MECHANICAL BEHAVIOR

BACKGROUND OF THE INVENTION

The invention concerns intervertebral disc prostheses.

European Patent No. 0356112 discloses an intervertebral disc prosthesis comprising two plates and a cushion of compressible material interposed between and fixed to them. Such a prosthesis permits substantial mobility between the two adjacent vertebrae. It can in particular be subjected to movements of compression between the two vertebrae, and movements of torsion on three mutually perpendicular axes. Its mechanical behavior thus comes close to that of a healthy natural intervertebral disc. However, it has the particular disadvantage that the lateral stresses of each vertebra on the disc in a direction perpendicular to the longitudinal direction of the spine are transmitted in their entirety to the other vertebra, which is not the case in a real healthy disc. These shearing stresses are detrimental.

It is an object of the invention to make a disc prosthesis which more closely imitates and approximates the mechanical properties of a healthy natural intervertebral disc.

SUMMARY OF THE INVENTION

With a view to achieving this object, the invention provides an intervertebral disc prosthesis comprising two plates and a cushion interposed between the plates, the cushion comprising a compressible body which has ends in contact with the plates, where at least one of the ends is freely displaceable relative to the associated plate in a direction parallel to the plate.

By this means it is possible to avoid excessive lateral stresses between the two vertebrae in a direction perpendicular to the longitudinal direction of the spine. The behavior of a healthy natural disc is thus more faithfully reproduced.

The end or each end of the body is advantageously lodged in a recess which is provided in one of the plates and which can form a lateral abutment for this end.

It is thus possible to limit the relative lateral displacements between the body and the plate or plates.

The end or each end advantageously has a face having a zone of contact with a face of the associated plate, said faces being arranged in such a way that the zone of contact has a surface area which increases when a stressing of the plate in the direction of the body increases.

Thus, for the lowest compression values, the mechanical reaction of the prosthesis upon compression of the body varies very little as a function of the change in dimension of the body in the direction of compression. To put it another way, the curve of the mechanical reaction of the prosthesis upon compression as a function of the variation in height of the cushion is barely inclined relative to the horizontal for low values of compression, and little force is applied at the start. This property reproduces that of a healthy natural disc.

The end or each end advantageously has a face in contact with a face of the associated plate, the two faces being curved in at least one common direction and being respectively concave and convex.

Thus, after a relative lateral displacement of the body and of the plate, these two faces ensure automatic centering of these elements, repositioning them in a coaxial arrangement. When the concave face has at least one radius of curvature greater than a corresponding radius of curvature of the convex face, this additionally provides a zone of contact having a variable surface area, as mentioned above.

The body advantageously comprises a viscoelastic material, in particular silicone.

Thus, during compression, this material behaves such that the aforementioned curve has a hysteresis form, which brings the behavior of the prosthesis even closer to that of the healthy natural disc.

The prosthesis advantageously comprises a fluid interposed between the plates.

The fluid, particularly when it is compressible, further accentuates the hysteresis form.

The fluid is advantageously in contact with the plates.

The fluid advantageously extends about the periphery of the body.

The prosthesis advantageously comprises a chamber enclosing the fluid and arranged in such a way that it has a surface area of transverse section parallel to the plates which is substantially invariable when a stress moving the plates toward one another varies.

The prosthesis is advantageously intended for the lumbar region of the spine.

Other characteristics and advantages of the invention will become more apparent from the following description of the preferred embodiments given as nonlimiting examples.

BRIEF DESCRIPTION OF THE DRAWINGS

FIG. 1 is a perspective view of a prosthesis according to the invention;

FIG. 2 shows the prosthesis from FIG. 1 in axial section on the plane II—II;

FIG. 3 is a larger-scale view of a detail D from FIG. 2;

FIG. 4 is a curve indicating the compression force F exerted by the two plates on the cushion as a function of the variation in the distance separating them;

FIG. 5 is a sectional view of a detail of an alternative embodiment of the prosthesis; and FIG. 6 is a simplified view analogous to FIG. 2, showing a second alternative embodiment.

DETAILED DESCRIPTION OF THE INVENTION

FIG. 1 shows an intervertebral disc prosthesis 2 according to the invention particularly intended for the lumbar region of the vertebral column of the human body. The prosthesis 2 comprises two flat plates 4 having the general shape of a bean with a posterior hilum in plan view. Each plate 4 comprises a central circular panel 6 and a border 8 extending about the periphery of the panel 6 in the plane thereof. At rest, the two plates 4 extend parallel to each other, at a distance facing each other, with their contours in alignment. On each plate 4, the border 8 and the panel 6 each have a groove 17 for receiving a seal.

The disc prosthesis 2 comprises a cushion or intermediate part 10 interposed between the two plates 4. The cushion comprises a solid compressible body 12, here made of viscoelastic material, for example silicone. This body has a Shore-A hardness advantageously between about 60 and 100, in this case approximately 80. The body 12 has a shape of revolution about its main axis 14. It has a cylindrical lateral face 16 and two axial end faces 18 generally perpendicular to the axis 14 and of slightly convex spherical shape.

Each face 18 thus has two identical curvatures in mutually perpendicular planes. The body 12 is disposed coaxially with the panels 6. Each panel 6 has a plane inner central face 20 perpendicular to the axis 14 and in contact with one of the respective axial ends 18 of the body 12. Thus, the convex spherical face 18 of the body rests on the plane face 20 of the plate. The body 12 rests without anchorage on each of the plates 4 that it is movable relative to each of these plates in a direction parallel to the plates, or perpendicular to the main axis 14. Given the compression of the body 12 exerted by the plates 4, and the form of the faces of the plates and the body, the mobility in this direction is manifested by a rolling movement, optionally without sliding, of each axial end 18 of the body on the face 20 of the plate with which it is in contact. The body 12 thus rolls between the two plates. The two plates are thus displaced laterally relative to each other while remaining parallel, if necessary. This therefore avoids transmission of lateral stresses from one vertebra to the other.

The cushion 10 additionally comprises a bellows 22. The bellows 22 coaxially surrounds the body 12 at a distance therefrom. The bellows 22 has a shape symmetrical in revolution about the axis 14. Its wall profile comprises corrugations 24 which allow the length of the bellows 22 to be varied in the axial direction 14 without any appreciable variation to the surface area of its cross section transverse to the axis 14. The bellows 22, like the plates 4, may be made of titanium or titanium alloy so that it has a certain axial rigidity and forms a compression spring. The bellows can also be deformed in a direction perpendicular to the axis 14 or be twisted about the axis 14 or any axis perpendicular thereto.

At its two axial ends, the bellows 22 has edges bonded to respective edges of the panels 6 projecting from the inner face 20. The bonding is leaktight so that the bellows 22 and the two panels 6 define a variable-volume leaktight chamber extending around the body 12. This chamber encloses a fluid, for example a gas such as air. The corrugations 24 nearest the body 12 extend at a distance from it in order to permit free circulation of the gas from one panel 6 to the other.

As shown, the bellows 22 has ten convolutions, with eight outer crests in addition to the two crests attached to the plates. The outer diameter is about 30 mm and the inner diameter is about 17 mm. Its height, when the prosthesis is not loaded, measures about 10 mm. The wall of the bellows can be produced using one, two or three sheets each measuring about 0.1 mm in thickness. The sum of the thicknesses of the sheets forms the thicknesses of the wall. The bellows here has an inherent strength of about 1.6 N/mm.

Each border 8 includes two lugs 25 projecting from an outer face of the plate 4 perpendicularly to the plane of the plate. Each lug 25 has an orifice 27 transversing through it in the direction of the center of the panel and, a spherical recess directed away from the plate 4 on one face of the lug 25. The orifices 27 are able to receive a bone screw 26 having a head 28 whose lower face has a male spherical shape cooperating with the female recess of the lug 25 so as to allow free orientation of the screw 26 relative to the associated lug.

For short-term anchoring of the disc prosthesis 2 in the spine, the screws 26 can be anchored in the spondylus of the vertebrae adjacent to the disc to be replaced.

A "long-term" anchorage may also be envisaged in which the surfaces of the plates 4 in contact with the adjacent vertebrae are covered with hydroxyapatite or any other substance known per se for stimulating bone growth. Prior to being covered, the surfaces can be treated to obtain a more or less porous surface condition, with anchoring points for the bone tissue, in order to ensure a better interface with said bone tissue.

FIG. 4 shows the path of the curve C indicating the intensity of a compression force F exerted on the cushion 10 (that is to say on the two plates 4), disregarding their deformability, which is virtually nil, in the axial direction 14, as a function of the variation in the length l of the cushion in the axial direction 14 (or in the distance between the two plates). This curve also represents the mechanical reaction R of the cushion 10 under the same conditions. This curve C is not linear. Moreover, it has a hysteresis form: the curve Ca indicating the increase in the compression F starting from the zero origin being distinct from the curve Cd indicating the decrease in compression F up to the origin, and extending entirely above it. This pronounced hysteresis form is due principally to the viscoelastic material of the body and secondarily to the combination of the body 12 and the fluid in the cushion 10.

In addition, the curve Ca, relating to the increase in the compression force F, exhibits a gently sloping portion Ca1 from the origin O, then a more heavily sloping portion Ca2. The curve Cd illustrating the decrease in compression F has, for the highest values of the force F, a portion Cd1 with a pronounced slope and then, for the lowest values of the force F, a portion Cd2 with less slope. The presence of a portion with slight slope near the origin for curves Ca and Cd is due principally to the configuration of the contact faces 18, 20 of the body 12 and of the plates 4, which means that the surface area of the zone of mutual contact between each plate and the body, generally of disc shape, increases when the force F increases. This increase takes place until the maximum surface area of the contact zone is reached, when the whole face 18 is touching the plate 4.

The connection points Ja and Jd respectively form the junction between the curves Ca1 and Ca2 and Cd1 and Cd2. On the curve Ca, the point Ja corresponds to the force F at which the maximum contact surfaces between the plates and the body are reached. Likewise, on the curve Cd, the point Jd corresponds to the force at which these surfaces cease to be at their maximum.

The prosthesis can be configured such that the point Ja corresponds to a value Δ1 between 25% and 75% of the maximum variation in length envisaged for the prosthesis during use.

Referring to FIG. 5, in an alternative embodiment (otherwise having the other characteristics of the prosthesis in FIG. 1), the face 20 of each plate 4 opposite the body 12 has a recess 32, in this case a U-shaped recess, forming a lateral abutment in which the corresponding axial end 18 of the body fits. The relative lateral displacements of the body 12 with respect to each plate 4 are thus limited to a certain range, or even totally barred.

In the alternative embodiment shown in FIG. 6, the face 20 can be curved and concave in one or both directions, as shown, and the face 18 can be curved and convex in the corresponding direction(s), the radius of curvature of the face 20 being greater, for each direction, than that of the face 18 in the corresponding direction. The two faces 18, 20 are spherical as shown. The radii of curvature of the surfaces 18 and 20 will, for example, be within the range of about 70 and 80 mm and between about 140 and 200 mm respectively. Such an arrangement makes the two faces to be centered automatically while at the same time permitting a relative lateral displacement of the body 12 with respect to the plate in any direction perpendicular to a longitudinal direction of the spine.

In the embodiment in FIG. 2, the two ends of the body 12 have a contact surface 18 with the associated plate of variable surface area, making it laterally movable relative to the body.

By contrast, in the alternative embodiment shown in FIG. 6, only one of the ends 18 of the body 12 exhibits this property. The other end, being the lower end in FIG. 6, has a plane circular shape with an invariable contact zone 19 with the associated plate and fixed relative to the latter.

Of course, many modifications can be made to the invention without departing from the scope thereof.

The fluid of the leaktight chamber can be a liquid, or even a mixture of a liquid and of a gas, the latter for example being weakly soluble in the liquid.

The body 12 can have an elliptic shape in cross section transverse to the axis 14.

The inner face 20 of the plates 4 can be convex, the axial end face 18 of the body 12 being plane, or concave with a greater radius of curvature than that of the face 20 of the plate. The two contacting faces of the plate and of the body can be convex. The curvature of the faces can be limited to a single plane. The characteristics relating to the bellows 22 (spring effect, distance from body 12) can be used independently of the other characteristics.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Intervertebral disc prosthesis comprising:
   two plates having inner faces; and
   a cushion interposed between the plates, the cushion comprising an elastic body having ends in contact with the inner faces of the plates, wherein at least one of the ends is freely displaceable relative to the associated plate in a direction parallel to the plate, and wherein, prior to loading, the at least one of the ends has a radius of curvature less than that of the inner face of the associated plate.

2. Prosthesis according to claim 1, wherein at least one end of the body is lodged in a recess provided in one of the plates forming a lateral abutment for the at least one end.

3. Prosthesis according to claim 1, wherein at least one end has a face having a zone of contact with a face of the associated plate, wherein the zone of contact has a surface area which increases when a stressing of the plate in the direction of the body increases.

4. Prosthesis according to claim 1, wherein at least one end has a face in contact with a face of the associated plate and the end face and the plate face are curved in at least one common direction being respectively convex and concave.

5. Prosthesis according to claim 1, wherein the body comprises a viscoelastic material.

6. Prosthesis according to claim 1, further comprising a fluid interposed between the plates.

7. Prosthesis according to claim 6, wherein the fluid is in contact with the plates.

8. Prosthesis according to claim 7, wherein the fluid extends about the periphery of the body.

9. Prosthesis according to claim 8, further comprising a chamber extending about the periphery of the body and enclosing the fluid, wherein a surface area of a transverse section of the chamber parallel to the plates is substantially invariable when a stress moving the plates toward one another varies.

10. Prosthesis according to claim 1, wherein the prosthesis is an intervertebral lumbar disc prosthesis.

11. Prosthesis according to claim 5, wherein the viscoelastic material is silicone.

12. Intervertebral disc prosthesis comprising:
    two plates;
    a cushion interposed between the plates, the cushion comprising a compressible body having ends in contact with the plates, wherein at least one of the ends is freely displaceable relative to the associated plate in a direction parallel to the plate;
    a fluid interposed between the plates, the fluid being in contact with the plates; and
    a chamber extending about the periphery of the body and enclosing the fluid.

13. Prosthesis according to claim 12, wherein at least one end of the body is lodged in a recess provided in one of the plates forming a lateral abutment for the at least one end.

14. Prosthesis according to claim 12, wherein at least one end has a face having a zone of contact with a face of the associated plate, wherein the zone of contact has a surface area which increases when a stressing of the plate in the direction of the body increases.

15. Prosthesis according to claim 12, wherein at least one end has a face in contact with a face of the associated plate and the end face and the plate face are curved in at least one common direction being respectively convex and concave.

16. Prosthesis according to claim 12, wherein the body comprises a viscoelastic material.

17. Prosthesis according to claim 16, wherein the viscoelastic material is silicone.

18. Prosthesis according to claim 12, wherein the fluid extends about the periphery of the body.

19. Prosthesis according to claim 18, wherein a surface area of a transverse section of the chamber parallel to the plates is substantially invariable when a stress moving the plates toward one another varies.

20. Prosthesis according to claim 12, wherein the prosthesis is an intervertebral lumbar disc prosthesis.

21. Intervertebral disc prosthesis comprising:
    two plates having inner faces;
    a cushion interposed between the plates; and
    a chamber extending about the periphery of the cushion;
    wherein the cushion comprises a compressible body having ends in contact with the inner faces of the plates;
    at least one of the ends is freely displaceable relative to the associated plate in a direction parallel to the plate; and
    prior to loading, the at least one of the ends has a radius of curvature less than that of the inner face of the associated contacting plate.

22. The prosthesis according to claim 21, wherein at least one end has a face having a zone of contact with a face of the associated plate, and the zone of contact has a surface area which increases when a stressing of the plate in the direction of the body increases.

23. The prosthesis according to claim 21, further comprising a liquid within the chamber.

* * * * *